United States Patent [19]

Nagasuna et al.

[11] Patent Number: 5,389,722
[45] Date of Patent: Feb. 14, 1995

[54] HYDROPHILIC RESIN AND METHOD FOR PRODUCTION THEREOF

[75] Inventors: Kinya Nagasuna, Himeji; Kunihiko Ishizaki, Suita, both of Japan

[73] Assignee: Nippon Shokubai Co., Ltd., Osaka, Japan

[21] Appl. No.: 70,765

[22] Filed: Jun. 3, 1993

[30] Foreign Application Priority Data

Jun. 5, 1992 [JP] Japan .................. 4-145494
Jun. 5, 1992 [JP] Japan .................. 4-145495
Feb. 15, 1993 [JP] Japan .................. 5-025525

[51] Int. Cl.$^6$ .............................. C08F 8/00
[52] U.S. Cl. ............................ 525/55; 525/328.2; 525/328.4; 525/328.5; 525/328.9; 525/329.4; 525/329.5; 525/329.7; 525/330.1; 525/330.3; 526/273; 526/287; 526/288; 526/303.1; 526/307.2; 526/307.3; 526/307.4; 526/307.5; 526/307.6; 526/307.7; 526/317.1; 526/318; 526/318.4; 526/318.41; 526/318.42; 526/318.44; 526/318.5; 526/320; 526/323.1; 526/323.2; 526/325; 526/328.5; 526/329.5; 526/329.6

[58] Field of Search ........... 526/323.1, 318.44, 323.2, 526/318.4, 317.1, 318.41, 318.5, 320, 325, 328.5, 307.4, 318.42, 329.5, 329.6, 273, 287, 288, 303.1, 307.2, 307.3, 307.5, 307.6, 307.7, 318; 523/307; 524/502; 525/55, 328.2, 328.4, 328.5, 328.9, 329.4, 329.5, 329.7, 330.1, 330.3

[56] References Cited

U.S. PATENT DOCUMENTS

| | | | |
|---|---|---|---|
| 4,351,922 | 9/1982 | Yoshida et al. | 526/323.2 X |
| 4,590,068 | 5/1986 | Berthet et al. | 526/323.2 X |
| 4,658,002 | 4/1987 | Tschang et al. | 526/264 |
| 4,803,252 | 2/1989 | Kida et al. | 526/323.2 X |
| 4,957,984 | 9/1990 | Itoh et al. | 526/240 |
| 5,036,149 | 7/1991 | Obrecht et al. | 526/323.2 |
| 5,089,579 | 2/1992 | Sutter et al. | 526/323.2 |

FOREIGN PATENT DOCUMENTS

| | | |
|---|---|---|
| 0036294 | 9/1981 | European Pat. Off. . |
| 4020780 | 8/1991 | Germany . |
| 58-180233 | 10/1983 | Japan . |
| 59-189103 | 10/1984 | Japan . |
| 61-16903 | 1/1986 | Japan . |
| 1-292004 | 11/1989 | Japan . |
| 2-132103 | 5/1990 | Japan . |
| 2-153903 | 6/1990 | Japan . |
| 0126710 | 4/1992 | Japan ............... 526/323.2 |

*Primary Examiner*—Judy M. Reddick
*Attorney, Agent, or Firm*—Burns, Doane, Swecker & Mathis

[57] ABSTRACT

A hydrophilic resin is produced by a method which comprises copolymerizing a hydrophilic unsaturated monomer with 0.001 to 50 mol %, based on the amount of said monomer, of a first cross-linking agent possessing a structural unit represented by the general formula (I):

$$CH_2=CHOO(CH_2CH_2COO)_n \qquad (I)$$

wherein n represents an integer of at least 1, and then heat-treating the product of the copolymerization. An absorbent resin is produced by a method which comprises treating the hydrophilic resin obtained as described above, in the surface region of the resin, in the presence of a third cross-linking agent capable of reacting with the functional group of the hydrophilic resin.

The absorbent ratio of the absorbent resin with respect to physiological saline solution is able to be increased to at least 20 g/g as compared to its original level by being heat-treated at a temperature of 150° C. for 30 minutes.

24 Claims, 1 Drawing Sheet

HYDROPHILIC RESIN AND METHOD FOR PRODUCTION THEREOF

BACKGROUND OF THE INVENTION

1. Field of the Invention

This invention relates to a method for the production of a hydrophilic resin and to a novel absorbent resin.

More particularly, this invention relates to a method for the production of a hydrophilic resin characterized by the steps of copolymerizing a hydrophilic unsaturated monomer with a cross-linking agent possessing a specific structural unit and subjecting the resultant crosslinked copolymer to a heat treatment and to an absorbent resin capable of changing the absorption capacity thereof upon being heated.

The method of production according to this invention offers a convenient solution to the various problems encountered by the conventional method of production, simplifies the process of production, and not only realizes a prominent improvement in productivity but also enables the produced hydrophilic resin to have various improved properties.

Further, the absorbent resin of this invention, though dry in constitution, is endowed with the heretofore unattainable characteristic of having the absorption capacity thereof changed upon being heated. Thus, it promises utility in a wide range of novel applications. The absorbent resin of this type, after being used to capacity, can be easily solubilized and decomposed and therefore discarded easily and safely.

2. Description of the Prior Art

Generally, the hydrophilic resins are broadly classified by solubility under water-soluble resins and absorbent resins.

The water-soluble resins which have been heretofore known to the art include polysodium acrylate (JP-B-48-42,466 and JP-B-42-9,656), polyacrylic acid and polyacryl amide (JP-A-54-145,782 and JP-A-57-18,652), polymer of 2-acryl amide-2-methyl propane sulfonic acid (JP-A-2-173,108), partially hydrolyzed polyacryl amide (JP-A-52-137,483), acrylic acid-acryl amide copolymer (JP-A-59-15,417), (meth)acrylic acid-itaconic acid copolymer (JP-A-58-91,709), and polyvinyl alcohol, for example.

The absorbent resins are water-insoluble hydrophilic resins which are gelled by absorbing water and have found extensive utility in the field of hygienic articles such as disposable diaper and sanitary napkins, in the field of agriculture and forestry, and in the field of civil engineering, for example.

The absorbent resins of this type which have been known heretofore to the art include partially neutralized cross-linked polyacrylic acids (JP-A-55-84,304, JP-A-55-108,407, JP-A-55-133,413, JP-A-56-84,632, and JP-A-57-34,101), hydrolyzed starch-acrylonitrile graft polymer (JP-A-46-43,995), neutralized starch-acrylic acid graft polymer (JP-A-51-125,468), saponified vinyl acetate-acrylic ester copolymer (JP-A-52-14,689), hydrolyzed acrylonitrile copolymer or acryl amide copolymer (JP-A-53-15,959) or cross-linked compounds thereof, cross-linked cationic monomers (JP-A-58-154,709 and JP-A-58-154,710), and crosslinked copolymer of 2-acryl amide-2-methyl propane sulfonic acid with acrylic acid (JP-A-58-2,312), for example.

In the methods used for producing these hydrophilic resins, the procedure which comprises preparing the solution of a hydrophilic unsaturated monomer in a solvent such as water, subjecting the solution to aqueous solution polymerization or reversed-phase suspension polymerization thereby obtaining a gel-like polymer, and optionally drying the polymer is generally employed. As a natural consequence, the production of such a hydrophilic resin is required to handle a gel-like polymer. Since the gel-like polymer which is not cross-linked at all or is cross-linked only sparingly is extremely soft and viscous, however, it poses numerous problems to various steps of the process of production such as polymerization, pulverization, conveyance, and drying.

As a solution of these problems, it is possible to consider adopting a method for enabling the hydrophilic resin to acquire a greatly increased cross-linked density. This method is capable of solving the problems mentioned above because it causes the gel-like polymer to acquire increased gel strength and consequently a lowered viscosity. The incorporation of a high degree of cross-linking to the water-soluble resin has no relevance in the first place. Further, the useless increase of cross-linked density in the absorbent resin only brings about a great decrease in the resin's absorption capacity and keeps the resin from acquiring the desired high absorption capacity. In many cases, the conspicuous decrease of the absorption capacity renders the absorbent resin no longer capable of withstanding the impact of actual use.

Further, it has been heretofore customary for the absorption capacity of a given absorbent resin to be adjusted exclusively by altering the conditions of production such as the amount of a cross-linking agent used in the production of the polymer. It has been impossible to impart an increased absorption capacity to the absorbent resin in the dry state in which the resin is obtained as a finished product. A manufacturing process for obtaining an absorbent resin having a specific absorption capacity, therefore, must control complicated and delicate conditions of production. Generally, consumers of absorbent resins, such as diaper producers, are not in a position to effect a desired adjustment in the absorption capacity of an absorbent resin and therefore, have no alternative but to procure absorbent resins having widely varying absorption capacity fit for numerous uses.

The technique of cross-linking the surface region of an absorbent resin has hitherto been known to the art in order to improve the absorption properties of an absorbent resin on ideally balanced levels contrary to these absorbent resins. Further, a number of methods have been proposed to date for the realization of this improvement.

For example, methods which use a polyhydric alcohol (JP-A-58-180,233 and JP-A-61-16,903), a method which uses a polyglycidyl compound, polyaziridine compound, polyamine compound, or polyisocyanate compound (JP-A-59-189,103), a method which uses a glyoxal (JP-A-52-117,393), methods which use polyvalent metals JP-A-51-136,588, JP-A-61-257,235, and JP-A-62-7,745), methods which use silane coupling agents (JP-A-61-211,305, JP-A-61-252,212, and JP-A-61-264,006), a method which uses an epoxy compound and a hydroxy compound (JP-A-2-132,103), and a method which uses an alkylene carbonate (DE-4020780) separately as a cross-linking agent have been known to the art. Besides, methods which resort to the presence of an inert inorganic powder (JP-A-60-163,956 and JP-A-60-255,814), a method which resorts to the presence of a dihydric alcohol (JP-A-1-292,004), and a method which resorts to the presence of water and an ether compound (JP-A-2-153,903) separately during the process of the cross-linking reaction have been also known to the art.

Though these methods improve the balance of various properties of an absorbent resin to a certain extent, the improvement obtained hardly deserves to be called satisfactory. The improved absorbent resins which are produced by these methods have room for further enhancement in quality. Particularly in recent years, the need to develop a resin which maintains at a high level, the absorption capacity without load, one of the fundamental physical properties inherent in the conventional absorbent resin, and also excels in the absorption properties under load, particularly the absorption capacity under load, has come to find widespread recognition. As a matter of course, the absorption capacity without load and the absorption capacity under load generally contradict each other. The heretofore known conventionally techniques for the surface cross-linking of an absorbent resin are such that they cannot fully satisfy this need.

In addition to the problems regarding the production and properties on use of a hydrophilic resin, the problem of safe disposal of a used hydrophilic resin has attracted increasing interest as a public issue.

In the discarding of disposable diapers which are frequently used in huge quantities, for example, the practice of burying such used disposable diapers in soil is now popular. The gel of an absorbent resin which, unlike pulp, has a cross-linked structure persists a long time in an undecomposed state in soil. Thus, techniques for liquefying the absorbent resin by irradiating the gel of the absorbent resin with an ultraviolet light (JP-A-1-231,983) and adding an oxidizing agent to the gel (JP-A-1-284,507), for example, have been proposed. These methods, however, entail a complicated procedure and, moreover, fail to allow sufficient decomposition of the absorbent resin.

The present invention is accomplished in order to prove such situation, so an object of this invention is to provide a convenient method for the production of a hydrophilic resin excellent in various properties, which method allows the individual steps of the process of production to proceed stably at all times irrespective of the kind of hydrophilic resin.

Another object of this invention is to provide a novel absorbent resin which, even in the form of a finished product, enables the absorption capacity thereof to be elevated at will.

Yet another object of this invention is to provide an absorbent resin which exhibits as high an absorption capacity under load as in the absence of load and, particularly when it is used as a material for sanitary articles, exhibits ideal properties and a method for the production of the absorbent resin.

Still another object of the present invention is to provide an absorbent resin capable of being decomposed when it is wasted.

SUMMARY OF THE INVENTION

The objects mentioned above are accomplished by a method for the production of a hydrophilic resin comprising the steps of copolymerizing a hydrophilic unsaturated monomer with an amount in the range of from 0.001 to 50 mol%, based on the amount of the monomer, of a first cross-linking agent possessing a structural unit represented by the general formula (I):

$$CH_2=CHCOO\text{-}(CH_2CH_2COO)_n\text{-} \quad (I)$$

wherein n represents an integer of at least 1, and subsequently heat-treating the resultant product of copolymerization.

These objects are accomplished by a method for the production of a hydrophilic resin comprising the steps of copolymerizing a hydrophilic unsaturated monomer with an amount in the range of from 0.001 to 50 mol%, based on the amount of the monomer, of a first cross-linking agent possessing a structural unit represented by the general formula (I):

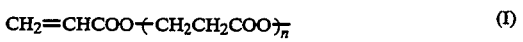

$$CH_2=CHCOO\text{-}(CH_2CH_2COO)_n\text{-} \quad (I)$$

wherein n represents an integer of at least 1, and treating the resultant hydrophilic resin in the presence in the surface region thereof of a third cross-linking agent capable of reacting with the functional group of the hydrophilic resin.

The objects are further accomplished by an absorbent resin which allows the absorption capacity of its own with respect to physiological saline solution to be increased to at least 20 (g/g) as compared to initial level by being heat-treated at a temperature of 150° C. for 30 minutes.

The objects are further accomplished by an absorbent resin wherein the absorption capacity thereof with respect to physiological saline solution is not less than 55 g/g and the absorption capacity thereof with respect to artificial urine under load is not less than 30 ml/g.

The method of this invention purports to obtain a hydrophilic resin possessing the required physical properties, such as an absorbent resin possessing the required absorption capacity or a water-soluble resin exhibiting viscosity in a desired range, by polymerizing the hydrophilic unsaturated monomer with the aid of the first cross-linking agent, subsequently heat-treating the resultant cross-linked polymer. The method of this invention enjoys such outstanding features as shown in (1) through (6) below.

(1) The polymerization proceeds uniformly without adhesion or cohesion of the hydrophilic polymer.
(2) The hydrophilic polymer can be finely divided uniformly during and after the process of polymerization.
(3) The produced polymer can be easily extracted from the polymerization vessel and can be easily transported to the next step of the process of production.
(4) At the step of drying, the polymer which is in the process of formation can be easily dried because it is in a finely divided and only sparingly aggregated state.
(5) The method allows easy production of an absorbent resin of a high absorption capacity capable of forming a gelled polymer which exhibits high levels in softness and viscosity.
(6) The method of production allows convenient production of a resin which has a high absorption capacity without load as one of the fundamental physical properties of an absorbent resin and which excels in absorption characteristics under load, especially in the absorption capacity under load, and the absorbent resin is ideally suited for use in such hygienic materials as disposable diapers and sanitary napkins.

Since this method of production allows the monomer to be uniformly polymerized and the polymer in the process of formation to be uniformly dried in addition to enjoying the various advantages mentioned above, the produced hydrophilic resin excels in various physical properties.

The absorbent resin of this invention which is produced by cross-linking the hydrophilic unsaturated monomer with the aid of the first cross-linking agent and further drying the cross-linked polymer possessing such outstanding features as shown in (1) through (3) below.

(1) This absorbent resin is a novel substance which is inherently dry and nevertheless capable of having its absorption capacity changed to a desired level by the application of heating.

(2) The production of the absorbent resin with a desired absorption capacity is accomplished by a convenient measure of adjusting the temperature of heating and the duration of heating.

(3) When the absorbent resin which has been gelled as a consequence of being use is discarded, it is easily decomposed by exposure to heating conditions. Thus, the gelled absorbent resin is easy to dispose of and fit for the preparation of compost.

DESCRIPTION OF THE PREFERRED EMBODIMENT

Figure 1:
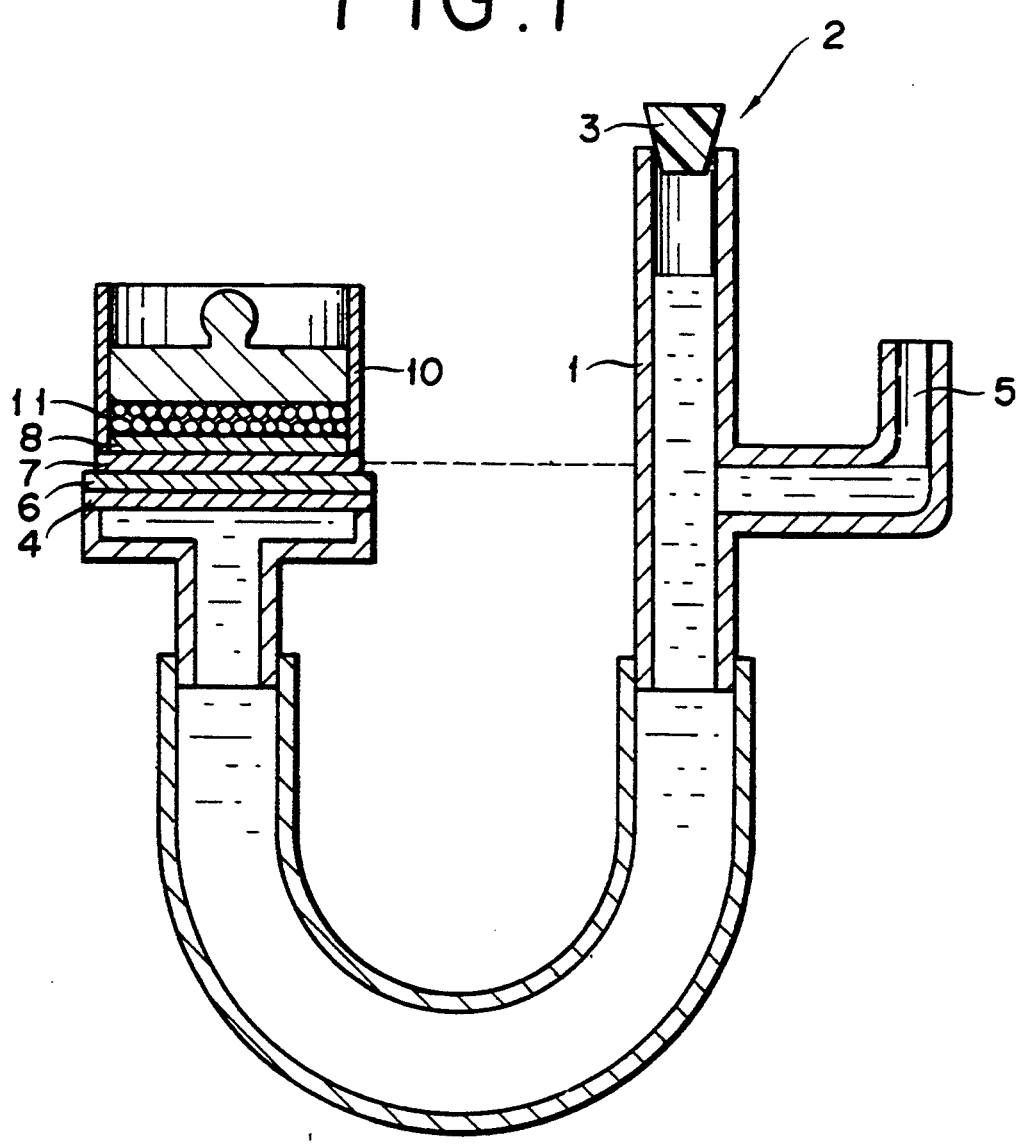
FIG. 1 is a cross-section of an apparatus used in this invention for the determination of absorption capacity under load.

In the method of this invention for the production of a hydrophilic resin, the first step comprises copolymerizing a hydrophilic unsaturated monomer and a first cross-linking agent (hereinafter referred to as "cross-linking agent (1)") having a structural unit represented by the general formula (I) thereby obtaining a cross-linked polymer originating in the cross-linking agent (1). Generally the cross-linked density of the cross-linked polymer which is formed by the cross-linking agent (1) is higher than the cross-linked density of the hydrophilic resin which is required by the invention.

The hydrophilic unsaturated monomer to be used in this invention has no particular restriction except for the sole requirement that it should be capable of forming a hydrophilic resin by polymerization. The hydrophilic unsaturated monomers which satisfy this requirement include acid group-containing hydrophilic unsaturated monomers and salts thereof such as acrylic acid, methacrylic acid, maleic acid, maleic anhydride, fumaric acid, crotonic acid, itaconic acid, $\beta$-acryloyloxy propionic acid, vinyl-sulfonic acid, styrene-sulfonic acid, 2-(meth)acrylamide-2-methyl propane sulfonic acid, 2-(meth)acryloyl ethane sulfonic acid, 2-(meth)acryloyl propane sulfonic acid, and sulfoethoxy polyethylene glycol mono(meth)acrylate; nonionic hydrophilic unsaturated monomers such as acrylamide, methacrylamide, N-ethyl (meth)acrylamide, N-n-propyl (meth)acrylamide, N-isopropyl (meth)acrylamide, N,N-methyl (meth)acrylamide, 2-hydroxyethyl (meth)acrylate, 2-hydroxypropyl (meth)acrylate, methoxy polyethylene glycol (meth)acrylate, polyethylene glycol mono(meth)acrylate, vinyl pyridine, N-vinyl pyrrolidone, N-acryloyl piperidine, and N-acryloyl pyrrolidine; and cationic hydrophilic unsaturated monomers such as N,N-dimethylaminoethyl (meth)acrylate, N,N-diethylaminoethyl (meth)acrylate, N,N-dimethyl-aminopropyl (meth)acrylate, N,N-dimethylaminopropyl (meth)acrylamide, and quaternary salts thereof, for example. One member or a combination of two or more members selected from the group of hydrophilic unsaturated monomers cited above may be used. Such hydrophilic unsaturated monomers as methyl (meth)acrylate, ethyl (meth)acrylate, and vinyl acetate which form a hydrophilic resin in consequence of the hydrolysis which occurs on the functional group of the monomer after the monomer has been polymerized may be otherwise used as a hydrophilic unsaturated monomer.

Among other hydrophilic unsaturated monomers cited above, those monomers having acrylic acid (salts thereof), methacrylic acid (salts thereof), 2-(meth)acryloyl ethane sulfonic acid (salts thereof), 2-(meth)acrylamide-2-methylpropane sulfonic acid (salts thereof), $\beta$-acryloyloxy propionic acid (salts thereof), methoxy polyethylene glycol (meth)acrylate, N,N-dimethylaminoethyl (meth)acrylate, and acrylamide as a main component thereof prove to be particularly preferable and the monomers having acrylic acid (salts thereof) as a main component thereof prove to be most preferable in terms of the ability to copolymerize with the cross-linking agent (1) and the various physical properties of the hydrophilic resin to be obtained.

When the acid group-containing hydrophilic unsaturated monomer such as acrylic acid is to be used in the form of a salt thereof, the basic substance to be used for neutralizing this monomer has no particular restriction except for the requirement that it should be of a type heretofore generally accepted for the purpose of neutralization. The basic substances which satisfy this requirement includes for example hydroxides and (hydrogen) carbonates of alkali metals, ammonia, organic amines, and hydroxides and (hydrogen) carbonates of alkaline earth metals. One member or a combination of two or more members selected from the group of basic substances cited above may be used. Such a basic substance for neutralization may be used during polymerization or after polymerization. In this case, the ratio of neutralization may be suitably selected generally in the range of from 0 to 100 mol%, depending on the desired quality of the resultant hydrophilic resin. When the hydrophilic resin is an absorbent resin, for example, the ratio of neutralization of the acid monomer is generally in the range of from 30 to 95 mol%, preferably in the range of from 40 to 90 mol%, and more preferably in the range of from 50 to 85 mol%. This invention contemplates having the cross-linked density thereof increased in the process of polymerization and, therefore, allows easy production of an unneutralized or partially neutralized hydrophilic resin with extremely strong viscosity.

In addition to the hydrophilic unsaturated monomer of the quality described above, a hydrophobic unsaturated monomer may be partially used. The hydrophobic unsaturated monomers which are effectively usable herein includes, for example, styrene, vinyl chloride, butadiene, isobutene, ethylene, propylene, stearyl (meth)acrylate, and lauryl (meth)acrylate. The amount of such a hydrophobic unsaturated monomer to be partly used as described above is preferably in the range of from 0 to 50 mol%, more preferably from 0 to 20 mol%, and most preferably 0 to 10 mol%, based on the total amount of monomer used.

The cross-linking agent (1) to be used in this invention has no particular restriction except for the sole requirement that it should possess a structural unit represented by the general formula (I) and should be capable of cross-linking a monomer. Specific forms of this cross-linking agent (1) include:

(A) Compounds of the type possessing at least two structural units of the general formula (I).

(B) Compounds of the type possessing at least one structural unit of the general formula (I) and at least one other polymerizing unsaturated group.

(C) Compounds of the type possessing at least one structural unit of the general formula (I) and at least one reactive functional group capable of reacting with the hydrophilic unsaturated monomer to be used.

The cross-linking agent (1) is generally easily synthesized by the use of β-acryloyloxy propionic acid having n=1 which is obtained by the dimerization of acrylic acid and/or an oligomeric acid which is a polymer having n of at least 2 (hereinafter referred to collectively as "acrylic acid oligomer") such as trimer, tetramer, octamer, etc. of acrylic acid.

The acrylic acid oligomer to be used for the synthesis of the cross-linking agent (1) is an α,β-ethylenically unsaturated acid represented by the general formula (II):

(II)

wherein n represents an integer of at least 1. For the synthesis of the cross-linking agent (1), a mixture of acrylic acid oligomers or a simple acrylic acid oligomer desirably having an integer approximately in the range of 1 to 10, preferably 1 to 5. It is particularly preferable to use an acrylic acid oligomer containing an oligomer having n=1 in a concentration in the range of from 50 to 100 mol%. As a matter of course, in this case, the acrylic acid oligomer may contain therein an acid having n=0, i.e. acrylic acid. The proportion of the acrylic acid to be contained in the acrylic acid oligomer is preferably not more than 50 mol%, preferably not more than 30 mol%, in view of the fact that the heat treatment given to the crosslinked polymer induces marked changes in the physical properties of a consequently obtained hydrophilic resin, specifically in the absorption capacity of the absorbent resin.

Examples of the cross-linking agent (1) which is effectively used herein are ester type cross-linking agents of acrylic acid oligomer obtained by the esterification of acrylic acid oligomers mentioned above with an alcohol, thio-ester type cross-linking agents of acrylic acid oligomer obtained by the thioesterification of the acrylic acid oligomers with a thiol, carbamic ester type cross-linking agents of acrylic acid oligomer obtained by the reaction with an isocyanate, amide type cross-linking agents of acrylic acid oligomer obtained by the reaction of the acrylic acid oligomers with an amine, and polyvalent metal salt type cross-linking agents of an acrylic acid oligomer obtained by the reaction of the acrylic acid oligomers with a polyvalent metal salt. The synthesis of this cross-linking agent (1) is carried out as by the conventional method. For example, it is effected by causing acrylic acid oligomers or acid chlorides or alkali metal salts of acrylic acid oligomers to react with (polyvalent) alcohols, (polyvalent) thiois, (polyvalent) amines, (polyvalent) isocyanates, polyvalent metals, (polyvalent) epoxy compounds, (polyvalent) aziridines, (polyvalent) oxazolines, or compounds having at least two such functinoal groups.

The cross-linking agent (1) for use in this invention is suitably selected in consideration of the range in which the absorption capacity of the absorbent resin is to be increased when the produced cross-linked polymer is heat-treated and the range in which the viscosity of the water-soluble resin is to be varied. It is permissible to use a plurality of such cross-linking agents (1) possessed of varying properties. Among other cross-linking agents (1) cited above, the ester type cross-linking agents of acrylic acid oligomers are particularly preferred for this invention. Of all the alcohols which can be effectively use for the esterification, polyhydric alcohols proves to be particularly preferred.

Of the ester type cross-linking agents ( 1 ) advantageously usable for this invention, those of the type (A) mentioned above include ethylene glycol di(β-acryloyloxy propionate), diethylene glycol di(β-acryloyloxy propionate), propylene glycol di(β-acryloyloxy propionate), triethylene glycol di(β-aryloyloxy propionate), tetraethylene glycol di(β-acryloyloxy propionate), polyethylene glycol di(βacryloyloxy propionate), neopentyl glycol di(β-acryloyloxy propionate), trimethylol propane di(β-acryloyloxy propionate), trimethylol propane tri(β-acryloyloxy propionate), glycerol tri(β-acryloyloxy propionate), pentaerythritol tetra(β-acryloyloxy propionate), pentaerythritol tri(β-acryloyloxy propionate), dipentaerythritol hexa(β-acryloyloxy propionate), and tripentaerythritol octa(β-acryloyloxy propionate), for example. ( The word "β-acryloyloxy propionate"used herein is the generic term for esters which are obtained with acrylic acid oligomers.)

In the ester type cross-linking agents (1) which are used advantageously for this invention, those of the type (B) mentioned above include, for example allyl (β-acryloyloxy propionate), polyethylene glycol monoallyl ether (β-acryloyloxy propionate), ethylene glycol mono(β-acryloyloxy propionate ) monoacrylate, 1,3-(β-acryloyloxy propionate ) monoacrylate, 1,2-propylene glycol mono(β-acryloyloxy propionate)monoacrylate, polyethylene glycol mono(β-acryloyloxy propionate)monoacrylate, trimethylol propane mono(β-acryloyloxy propionate)diacrylate, and trimethylol propane di(β-acryloyloxy propionate )monoacrylate. The acrylate moieties mentioned above in the cross-linking agents (1) to be used in the form of (B) may be substituted with other polymerizing functional groups such as methacrylates.

In the ester type cross-linking agents (1) which are used advantageously in this invention, those of the type (C) mentioned above include, for example, glycidyl (β-acryloyloxy propionate).

As a cross-linking agents which may a similar action to the cross-linking agents (1) mentioned above include, for example, those cross-linking agents which incorporate such structual unit as an azo bond, a peroxide bond, an acid anhydride bond, hexamethylene, tetramine unit, and acetaldehyde ammonia unit.

Generally the amount of the cross-linking agent ( 1 ) to be used in this invention is such that these cross-linking agents enable more cross-linking points to be introduced into the hydrophilic resin than are necessary for the required degree of cross-linking and, consequently, bring about a desirable effect on the component steps of the process for production of the hydrophilic resin such as, for example, polymerization, pulverization, conveyance, and drying. The total amount of these cross-linking agents to be used in this invention, though variable with the chemical structure of the cross-linking agent (1) used and the conditions of heat-treatment employed, generally falls in the range of from 0.001 to 50 mol%, preferably from 0.005 to 20 mol%, and most preferably from 0.01 to 5 mol%, based on the amount of the hydrophilic unsaturated monomer under treatment.

When the desired product of this invention is an absorbent resin requiring a cross-linked structure, it is permissible to use a second cross-linking agent (hereinafter referred to as "cross-linking agent (2)") in addition to the cross-linking agent (1) with a view to facilitating control of the cross-linked density after the heat treatment step.

The cross-linking agents heretofore known to the art may be cited as examples of the cross-linking agent (2). They include N,N'-methylene bis(meth)acrylamide, (poly)ethylene glycol di(meth)-acrylate, (poly)propylene glycol di(meth)acrylate, trimethylol propane tri(meth)acrylate, trimethylol propane di(meth)acrylate, poly(meth)allyloxy alkanes, glycerol acrylate methacrylate, (poly)ethylene glycol diglycidyl ether, ethylene glycol, polyethylene glycol, glycerin, pentaerythritol, ethylene diamine, polyethylene imine, and ethylene carbonate, for example. Further, when the second cross-linking agent is also used, the amount of the second cross-linking agent is preferably not more than 50 mol% to the cross-linking agent (1).

The polymerization of the hydrophilic unsaturated monomer mentioned above in this invention can be carried out in the form of bulk polymerization or precipitation polymerization. In view of the quality of the produced polymer and the ease with which the polymerization is controlled, the polymerization is preferably carried out on the hydrophilic unsaturated monomer prepared in the form of a solution. The solvent used in the system of polymerization has no particular restriction except for the requirement that it should be a liquid substance which is capable of dissolving the hydrophilic unsaturated monomer. The solvents which satisfy this requirement include, for example, water, methanol, ethanol, acetone, dimethyl formamide, and dimethyl sulfoxide. Among other solvents for the polymerization systems mentioned above, water proves to be particularly preferred. The aqueous solution of the hydrophilic unsaturated monomer thus prepared for the polymerization is allowed to contain therein a small amount of a hydrophilic organic solvent. When the hydrophilic unsaturated monomer is polymerized in the form of a solution, the concentration of the monomer in the solution has no particular restriction including the solution having part of the monomer separated as a precipitate. Generally, this concentration is preferably in the range of from 20% by weight to the saturation concentration.

Heretofore, it has been usual for the polymerization of a hydrophilic unsaturated monomer of a low concentration because its gel polymer is soft and the polymerization itself and the handling of the produced polymer are difficult. By the method of this invention which gives rise to a highly cross-linked structure while the polymerization is in process, the polymerization can be easily carried out over a wide range of monomer concentrations because the gel polymer acquires an enhanced gel strength.

Further, for the purpose of inducing graft polymerization and tackifying the monomer, the hydrophilic unsaturated monomer is allowed to incorporate therein such a hydrophilic polymeric substance such as starch, cellulose, a derivative thereof, polyvinyl alcohol, or polyacrylic acid (salts thereof) when it is subjected to polymerization. This hydrophilic polymeric substance, when necessary, may be used in a cross-linked form. While the monomer is in process of polymerization, it may be used in combination with a water-soluble chain transfer agent such as a hypophosphite (salts thereof), thiois, or thiol acids so that the produced cross-linked polymer may acquire a bigger change of physical properties as a consequence of the heat treatment.

The methods which are effectively usable for the purpose of the polymerization include radical polymerization by the use of a radical polymerization initiator and polymerization by the use of an active energy such as ultraviolet light or an electron beam. Of these methods, the radical polymerization using a radical polymerization initiator is preferably used for the purpose of allowing production of a hydrophilic resin which enjoys excellent quality.

The radical polymerization initiators heretofore known to the art are effectively usable for the radical polymerization mentioned above. They include, for example, persulfates such as potassium persulfate, ammonium persulfate, and sodium persulfate; organic peroxides such as t-butyl hydroperoxide, cumene hydroperoxide and benzoyl peroxide; hydrogen peroxide; azo compounds such as 2,2'-azo-bis(2-amidinopropane) dihydrochloride and azo-bis-isobutyronitrile; and chlorites, hypochlorites, cerium II salts, and permanganates. Among other radical polymerization initiators mentioned above, one member or a combination of two or more members selected from the group comprising persulfates, hydrogen peroxide, and azo compounds proves to be particularly preferred.

When an oxidizing radical polymerization initiator is used, it may be used in combination with a reducing agent so as to effect the polymerization in the form of redox polymerization. The reducing agents which are effectively usable for the purpose of this redox polymerization include, for example, (hydrogen) sulfites such as sodium sulfite and sodium hydrogen sulfite; thiosulfates such as sodium thiosulfate; metal salts such as cuprous sulfate and ferrous sulfate; organic reducing agents such as l-ascorbic acid; and amines such as aniline and monoethanolamine. When an azo radical polymerization initiator is used, it may be used in combination with ultraviolet light.

In the method of production according to this invention which gives rise to a highly cross-linked structure during the polymerization, the amount of the radical polymerization initiator to be used for the polymerization can be selected over a wide range because the aggregation or adhesion of the gel is repressed and the removal of the heat of polymerization is easily attained while the polymerization is in process. The radical polymerization initiator may be added either in a lump or piecemeal to the polymerization system. The amount of radical polymerization initiator used is generally in the range of from 0.001 to 2 mol%, preferably from 0.01 to 1 mol%, based on the amount of the unsaturated monomer.

As the method for the radical polymerization, any of the techniques known to the art can be adopted. The methods which are effectively usable include for example aqueous solution polymerizations such as cast polymerization which is carried out in a framework (JP-B-48-42,466), polymerization which is carried out on a belt conveyor (JP-A-58-49,714), polymerization which is carried out on a hydrogel polymer in the process of pulverization (JP-A-57-34,101, U.S. Pat. No. 4,625,001 and U.S. Pat. No. 5,124,416), and polymerization which is carried out under an increased pressure (JP-A-2-129,207), reversed-phase suspension polymerization (JP-B-59-37,003), reversed-phase emulsion polymerization (JP-A-63-90,510 and JP-A-63-90,537), polymerization which uses the monomer combined with a fibrous substrate (JP-A-2-242,975), precipitation polymerization (JP-A-58-84,819, JP-A-1-1,710, and JP-A-1-204,910), and bulk polymerization.

Further, reduced pressure, normal pressure and high pressure during polymerization and continuous, batch wise and semi-batch wise polymerization may be optionally adopted. And when the hydrophilic resin to be desired is a water-soluble resin, undesirable selfcrosslinking except the cross-linking agent (1) can be removed by controlling a monomer concentration, a polymerization initiator or an additive by known means.

By the method of production according to this invention, the produced gel polymer enjoys enhanced gel strength and lowered tackiness because the cross-linked polymer yet to be heat-treated is allowed to acquire a higher degree of cross-linking than the eventual hydrophilic resin. This invention, therefore, prevents the polymer in the process of formation from succumbing to such adverse phenomenon as adhesion or aggregation and enables the pulverization of the polymer gel which is optionally carried out to proceed uniformly and, consequently, allows the product to acquire outstanding physical properties due to the uniform removal of the heat of polymerization and the uniform agitation of the polymer. Even after the polymerization, the extraction of the produced polymer from the polymerization vessel and the filtration of the polymer from the dispersion are easily effected because the adhesion of the gel polymer to the wall of the polymerization vessel occurs only sparingly. Further, the conveyance of the product of polymerization from the step of polymerization to the subsequent step is easily effected. Moreover, the gel polymer of this nature can be uniformly dried.

This invention obtains a hydrophilic resin exhibiting various properties as desired such as, for example, an absorbent resin having a desired absorption capacity or a water-soluble resin having viscosity in a desired range by the procedure described above, which specifically comprises copolymerizing a hydrophilic unsaturated monomer with the cross-linking agent (1) thereby producing a cross-linked polymer of a higher cross-linking degree than the desired hydrophilic resin and then heat-treating the cross-linked polymer. Further, it is possible to generate a functional group originated from the cross-linking agent (1) separately into the hydrophrlic resin after heat-treatment.

The temperature at which the heat treatment intended to enhance the absorption capacity is to be carried out, though variable with the structure and the amount of consumption of the cross-linking agent (1) generally falls in the range of from 100° to 300 ° C., preferably from 120° to 200 ° C. If the temperature of heat treatment is less than 100 ° C., the changes produced in physical properties by the heat treatment are small and the effect of the use of the cross-linking agent (1) is not easily manifested. Conversely, if this temperature exceeds 300 ° C., the excess heat possibly impairs the quality of the hydrophilic resin, depending on the backbone of the polymer. Thus, the range of temperature requires due observance.

The duration of the heat-treatment generally is in the range of from one second to 100 hours, preferably within 10 hours, more preferably within 5 hours, and most preferably within 2 hours. The use of the cross-linking agent (1) in accordance with this invention allows easy control of the absorption capacity of the absorbent resin or the viscosity of the water-soluble resin, depending on the temperature and the duration of heat treatment, and enables the hydrophilic resin which is used normally at room temperature, to manifest physical properties stably and enjoy durability. The finished product obtained from one and the same cross-linked polymer is able to acquire various attributes by adjusting the temperature and the duration of heat treatment.

Further, although it varies depending on a temperature of heat-treatment, the absorption capacity or solubility usually increases remarkably by not more than 2 hours heat-treatment at a temperature of 120° to 200 ° C., and if it is further subjected to heat-treatment, the absorption capacity or solubility begins to decrease conversely. Therefore, according to the present invention, it is possible to obtain a hydrophilic resin having optional absorption capacity and solubility by controlling a temperature or time of the heat-treatment.

The pH value of the polymerization system during the heat treatment is in the range of from 2 to 11, preferably from 4 to 9. If the pH value deviates from the range mentioned above, the produced hydrophilic resin may call for neutralization as an aftertreatment or may even suffer from impairment of physical properties.

The timing of the heat-treatment and the form of the cross-linked polymer verging on the heat treatment are not particularly restricted. The cross-linked polymer may be in the form of a gel polymer fresh from polymerization, in the form of a dispersion in an organic solvent, or in the form of a dry solid, for example. The solids content of the cross-linked polymer which is ready for the heat treatment may be kept at a constant level or may be elevated by expelling the solvent through volatilization.

Incidentally, for the purpose of uniformly enhancing the absorption capacity or altering the viscosity, the gel polymer or dry polymer subjected to the heat treatment is preferably in the form of a film or particles having a large surface area. In the heat treatment of a particulate polymer, for example, the polymer is in the form of powder or gel having an average particle diameter of not more than 10 mm, preferably not more than 5 mm.

Specifically, the time for performing the heat treatment in the process of this invention after the step of polymerization is automatically fixed by the particular manner of operation of the heat treatment which is selected from among the procedure in which the heat treatment is performed simultaneously with the operation of drying at the step of drying, the procedure in which the powder after drying is directly subjected to heat-treatment, the procedure in which the heat-treatment is carried out at the step of surface cross-linking, the procedure in which the heat-treatment is carried out at the step of granulation, and the procedure in which the heat-treatment is initiated after incorporation of additives in the polymer, for example. The method of drying and the method of heat treatment are not particularly restricted but may be selected from among the measures which are known to the art.

In the operation of surface cross-linking of the absorbent resin, when the absorbent resin produced by the use of the cross-linking agent (1) is adopted and the heat-treatment is carried out, preferably, simultaneously with the surface cross-linking of this absorbent resin, the surface region of the individual particles of the resin can be cross-linked to a high degree and the absorbent resin itself can be made to acquire a high absorption capacity. Thus, the surface cross-linking operation according to this invention can impart a decisively large cross-link gradient to the particles of the resin and confer excellent absorption properties to the produced absorbent resin as compared with the conventional method.

To be specific, by the procedure described above which comprises copolymerizing a hydrophilic unsaturated monomer with 0.001 to 50 mol%, based on the amount of monomer, of a first cross-linking agent possessing a structural unit represented by the general formula (I), then directly drying or heat-treating the resultant hydrophilic resin, and treating the dried or heat-treated hydrophilic resin (hereinafter a hydrophilic resin treated with the third cross-linking agent is referred to a water-swellable cross-linked polymer) in the presence in the surface region thereof of a third cross-linking agent capable of reacting with the functional group of the hydrophilic resin (hereinafter referred to as "cross-linking agent (3)"), there can be obtained an absorbent resin which has the surface region thereof cross-linked to a high degree and which has a higher absorption capacity than the original water-swellable cross-linked polymer.

The amount of the functional group such as, for example, a carboxyl group which is possessed by a water-swellable cross-linked polymer treated with a cross-linking agent (3), one form of the aforementioned absorbent resin, has no particular restriction. It is preferable to be at least 0.01 equivalent weight based on 100 g of the water-swellable cross-linked polymer. In the case of a partially neutralized cross-linked polyacrylic acid, for example, the proportion of the unneutralized component of the polyacrylic acid is preferable to be in the range of from 1 to 60 mol%, more preferably from 10 to 50 mol%.

The water-swellable cross-linked polymer can be handled as a powder of discrete particles when the water content thereof is in the range of from 1 to 50%, preferably from 1 to 20%, and more preferably from 1 to 10%. For the sake of this water content, the reaction of polymerization mentioned above is generally followed by a step of drying. If the water content of the water-swelling cross-linked polymer exceeds 50%, the cross-linking agent (3) used in this invention possibly permeates the water-swellable crosslinked polymer to the extent of lowering the absorption capacity of the polymer and preventing the absorption properties of the polymer under load from being improved.

The water-swellable cross-linked polymer is preferably produced at a temperature in the range of 10° to 150 °C., more preferably 30 °C. to 120 °C. in the production procedure. If the production temperature exceeds above 150 °C., absorption capacity under load sometimes does not increase, even if the heat reaction with the below mentioned cross-linking agent (3).

As respects the shape of the water-swellable cross-linked polymer, this polymer can be used advantageously for this invention in the shape of irregularly broken fragments, spheres, fibers, rods, or roughly spherical beads, for example. In view of the diffusibility of liquid, the difficulty with which the powder is moved or separated from pulp, and the applicability of the powder to sanitary materials, the powder of irregularly broken fragments obtained by the aqueous solution polymerization and possessing an average particle diameter in the range of from 100 to 1,000 μm, preferably from 300 to 600 μm, is most advantageously used.

The method of this invention is thence completed by mixing the water-swelling cross-linked polymer having the functional group and obtained as described above with a third cross-linking agent (hereinafter referred to as "cross-linking agent (3)") capable of reacting with the functional group and then heat-treating the resultant mixture.

The cross-linking agent (3) which can react with the functional group and can be effectively used in this invention is a compound which has in the molecular unit thereof two or more functional groups capable of reacting with the functional group mentioned above. The third cross-linking agents which answer the description include, for example, if the water-swellable cross-linked polymer has carboxyl group, polyhydric alcohol compounds such as ethylene glycol, diethylene glycol, propylene glycol, triethylene glycol, tetraethylene glycol, polyethylene glycol, propylene glycol, 1,3-propane diol, dipropylene glycol, 2,2,4-trimethyl-2,3-pentadiol, polypropylene glycol, glycerin, polyglycerin, 2-butene-1,4-diol, 1,4-butane diol, 1,5-pentane diol, 1,6-hexane diol, 1,2-cyclohexane dimethanol, 1,2-cyclohexanol, trimethylol propane, diethanolamine, triethanolamine, polyoxy propylene, oxyethylene-oxypropylene block copolymer, pentaerythritol, and sorbitol; polyepoxy compounds such as ethylene glycol diglycidyl ether, polyethylene diglycidyl ether, glycerol polyglycidyl ether, diglycerol polyglycidyl ether, polyglycerol polyglycidyl ether, propylene glycol diglycidyl ether, and polypropylene glycol diglycidyl ether; polyamine compounds such as ethylene diamine, diethylene triamine, triethylene tetramine, tetraethylene pentamine, pentaethylene hexamine, and polyethylene imine; polyisocyanate compounds such as 2,4-tolylene diisocyanate and hexamethylene diisocyanate; polyoxazoline compounds such as 1,2-ethylene bisoxazoline; alkylene carbonate compounds such as 1,3-dioxolan-2-on, 4-methyl-1,3-dioxolan-2-on, 4,5-dimethyl-1,3-dioxolan-2-on, 4,4-dimethyl-1,3-dioxolan-2-on, 4-ethyl-1,3-dioxolan-2-on, 4-hydroxymethyl-1,3-dioxolan-2-on, 1,3-dioxan-2-on, 4-methyl-1,3-dioxan-2-on, 4,6-dimethyl-1,3-dioxan-2-on, and 1,3-dioxan-2-on, haloepoxy compounds such as epichlorohydrin, epibromohydrin, and α-methyl epichlorohydrin; and polyvalent metal compounds such as hydroxides and chlorides of zinc, calcium, magnesium, aluminum, iron, and zirconium.

For this invention, it is preferable to use as the cross-linking agent (3) one or more compounds selected from the group of compounds mentioned above. From the standpoint of the effect of surface cross-linking, it is particularly preferable to use one or more members selected from the group consisting of polyhydric alcohols, polyglycidyl compounds, polyamines, and alkylene carbonates.

The amount of the cross-linking agent (3) to be used in this invention, though variable with the particular kind of cross-linking agent to be used, is generally in the range of from 0.001 to 10 parts by weight, preferably from 0.01 to 5 parts by weight, based on 100 parts by weight of the solids in the water-swellable cross-linked polymer. When this amount is in the range just mentioned, the produced absorbent resin has excellent absorption characteristics under load. If the amount of the cross-linking agent (3) used exceeds 10 parts by weight, the excess tends to be uneconomical without producing any addition to the proper effect of cross-linking. If this amount is less than 0.001 part by weight, the effect of improving the absorption characteristics under load is difficult to attain.

In this invention, during the mixing of the water-swelling cross-linked polymer with the cross-linking agent (3), it is preferable to add water to the site of the mixing either simultaneously with or separately of the operation of mixing. In this invention, the amount of water to be used is generally within 20 parts by weight, more preferably in the range of from 0.5 to 10 parts by weight, based on 100 parts by weight of the solids in the water-swellable cross-linked polymer, though variable with the particular type, granularity, and water content of the water-swellable cross-linked polymer.

Further in this invention, it is permissible to use a hydrophilic organic solvent during the mixture of the water-swellable cross-linked polymer with the cross-linking agent (3). The hydrophilic organic solvents which are effectively usable for this purpose include, for example, lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane and tetrahydrofuran; amides such as N,N-dimethyl formamide; and sulfoxides such as dimethyl sulfoxide. The amount of such a hydrophilic organic solvent to be used is generally less than 20 parts by weight, desirably in the range of from 0.01 to 10 parts by weight, and preferably from 0.1 to 5 parts by weight, based on 100 parts by weight of the solids in the water-swellable cross-linked polymer, though the optimum amount thereof is variable with the particular kind and granularity of the water-swellable cross-linked polymer.

In this invention, the mixture of the water-swellable cross-linked polymer with the cross-linking agent (3) may be carried out with the water-swellable cross-linked polymer dispersed in an organic solvent. For the purpose of enabling the absorption characteristics under load obtained by this invention to be enhanced to the optimum extent, this mixing is advantageously effected by causing the cross-linking agent (3) optionally containing therein water and/or a hydrophilic organic solvent to be directly sprayed onto or added dropwise to the water-swelling cross-linked polymer. When the mixture involves use of water, it may be carried out in the presence of a water-insoluble powder of minute particles or a surfactant.

For a mixing device to be used advantageously for the mixture mentioned above, this device is required to produce a mixing force sufficient to ensure perfect homogenization. The mixing devices which are effectively usable in this invention include for example a cylindrical mixing device, a double-wall conical mixing device, a V-shaped mixing device, a ribbon type mixing device, a screw type mixing device, a fluidized-bed type mixing device, a rotary disc type mixing device, an air-current type mixing device, a twin-arm type kneader, an inner mixing device, a pulverizing kneader, a rotary type mixing device, and a screw type extruder.

In this invention, after the water-swellable cross-linked polymer has been mixed with the cross-linking agent (3), the resultant mixture is further heated for the purpose of cross-linking the surface region of the polymer.

When the heat-treatment is carried out after the addition of the cross-linking agent (3) in this invention, the temperature of this heat-treatment is generally set at a level higher than the temperature prevalent during the production of the water-swellable cross-linked polymer, though depending on the reactivity of the cross-linking agent (3) and the thermal hysteresis of the water-swellable cross-linked polymer. This temperature generally falls in the range of from 100° to 300° C, preferably from 130° to 230° C., and more preferably from 150° to 220° C. If the temperature of the heat-treatment is less than 100° C., the cross-linking agent (1) used for the formation of the water-swellable cross-linked polymer is difficult to effectively use and possibly fails to enhance the absorption characteristics under load. Conversely, if the temperature of the heat-treatment exceeds 300 ° C., the excessive temperature possibly causes impairment of the absorbent resin. Thus, the range of this temperature requires due observance.

The duration of the heat-treatment, though variable with the reactivity of the cross-linking agent (3) to be used, generally is in the range of from 1 second to 100 hours, preferably from one minute to 10 hours, and more preferably from 5 minutes to 2 hours.

The heat-treatment can be carried out by the use of an ordinary drying device or heating furnace. The devices which are effectively usable for this purpose include, for example, a groove type mixing and drying device, a rotary drying device, a desk type drying device, a fluidized-bed type drying device, an air-current type drying device, and an infrared drying device.

In addition to the method for the production of a hydrophilic resin described thus far, this invention provides a novel absorbent resin.

To be specific, by controlling the kind of the cross-linking agent (1), the amount of use thereof, and the conditions for the heat-treatment thereof, this invention allows production of an absorbent resin which in a dry state is able to have the absorption capacity thereof improved by heat-treatment. This absorbent resin of the present invention is a novel product in the sense that the resin, though obtained in a dry state, is able to have the absorption capacity thereof increased at will by heat-treatment.

For example, when the novel absorbent resin of the present invention in dry state can enhance the absorption capacity (g/g) thereof with respect to physiological saline solution not less than 20 (g/g) as compared to its original level by being heat-treated at a temperature of 150 ° C. for 30 minitues. The elevation of the absorption capacity by heating can be suitably controlled by the kind of the cross-linking agent (1) in the absorbent resin, the amount of the cross-linking agent (1) used, and the temperature and duration of the heat treatment. For a large change of absorbency after heat-treatment, drying of gel is preferably below 150 ° C., more preferably below 120 ° C.

The absorbent resin thus obtained wherein region of the surface is cross-linked is able to manifest such heretofore unattainable characteristics as an absorption capacity of at least 55 (g/g) in the absence of load with respect to physiological saline solution or an absorption capacity of at least 30 (ml/g) under load with respect to artificial urine.

The problem that the absorption capacity under load is lowered by an increase in the absorption capacity in the absence of load and conversely the absorption capacity in the absence of load is lowered by an increase in the absorption capacity under load has been always encountered heretofore. The absorbent resin which is obtained by this invention exhibits ideal absorption characteristics both in the absence of load and under load. Though the cause for this peculiar quality of the absorbent resin has not been determined, it may be logically explained by postulating that the cross-linking points distributed by the cross-linking agent (1) throughout the entire volume of the water-swellable cross-linked polymer are dissolved and severed during the thermal reaction due to the cross-linking agent (3) so as to heighten the cross-linked density in the surface region of the individual particles of the absorbent resin by using the cross-linking agent (3) and, at the same time, conversely lower the cross-link density inside the particles and, as a result, widen immensely the difference in cross-linked density between the surface region and the interior of the particles of the absorbent resin and give rise within the particles of the absorbent resin to a cross-linking having a peculiar density gradient never attained by the conventional method. Further, when the water-swellable cross-linked polymer is used in the form of irregularly broken fragments having the aforementioned specific average particle diameter, it can be turned into an absorbent resin which enjoys, in addition to the excellent absorption characteristics mentioned above such advantages as ideal diffusibility of liquid like urine and ample freedom from the adverse phenomena of migration and separation from pulp unlike the conventional absorbent resin and which, therefore, is ideal for use in sanitary materials.

Heretofore, the adjustment of the absorption capacity of a given absorbent resin has been attained solely by the producer of the absorbent resin effecting complicated and delicate control of the process of production. In the novel absorbent resin of this invention, since various properties thereof centering around the absorption capacity can be conveniently adjusted by means of the heat treatment, this invention enjoys the heretofore unattainable advantage that the producer will be no longer required to devise production conditions for each species of products and the users will be no longer compelled to purchase a large number of species of absorbent resin.

Further, the novel absorbent resin of this invention is such that when it is incorporated in such absorbent articles as disposable diapers and in other similar substratal articles during the fabrication thereof, the absorption capacity in a specific part of such articles in the process of formation can be varied by the heat treatment. Thus, the absorbent resin promises to find utility in numerous novel applications.

The novel hydrophilic resin of this invention produced by the use of the cross-linking agent (1) is such that it can be discarded easily after use. When the disposable diapers after use are incorporated in compost or disposed of by being buried in soil, for example, the hydrophilic resin contained therein can be easily solubilized by heating such discarded diapers or placing them under similar thermal conditions. Thus, safe disposal of the used disposable diapers is attained with ease.

The hydrophilic resin obtained by this invention may be incorporated therein deodorants, perfumes, inorganic powders, defoaming agents, pigments, dyes, hydrophilic short fibers, fertilizers, oxidizing agents, reducing agents, water, and salts, for example.

Now, this invention will be described more specifically below with reference to working examples. It should be noted, however, that the scope of this invention is not limited to these working examples. The physical properties of the hydrophilic resin to be described in the working examples represent data which have been determined by the methods shown below.

The properties of the absorbent resin have been determined by the following methods.

(a) Absorption capacity (without load).

This property was determined by uniformly placing 0.2 g of a given absorbent resin in a teabag-like pouch (40 ×150 mm) of nonwoven fabric, immersing the pouch containing the sample in an aqueous 0.9 wt % sodium chloride solution (physiological saline solution), removing the wet pouch from the solution after 60 minutes'standing therein, allowing the solution to strain out of the wet pouch for a prescribed length of time, weighing the pouch to find the weight ($W_1$), repeating the same procedure while avoiding use of the absorbent resin, finding the weight ($W_O$) of the wet pouch, and performing the calculation of the following formula 1.

$$\text{Absorption capacity (g/g)} = (\text{Weight } W_1 \text{ after absorption (g)} - \text{Weight } W_0 \text{ of blank (g)})/(\text{Weight of absorbent resin (g)}) \quad (1)$$

(b) Absorption capacity under load

With the aid of an apparatus constructed as illustrated in FIG. 1, this property was determined by plugging an upper mouth 2 of a buret 1 with a stopper 3, setting a measuring base 4 and an air inlet 5 at an equal level, placing a filter paper 7 on a glass filter 6 of a diameter of 70 mm located in the central part of the measuring base 4, fixing a non-woven fabric 8 at the lower terminal part of a supporting cylinder 10 of a diameter of 55 mm, uniformly scattering 0.2 g of a given absorbent resin 11 on the non-woven fabric 8, placing a load of 20 g/cm$^2$ on the scattered sample 11, mounting the total of non-woven fabric, absorbent resin, and load as held in the supporting cylinder on the filter paper 7 spread on the glass fiber 6, allowing artificial urine (containing 1.9% of urea, 0.8% of NaCl, 0.1% of CaCl$_2$, and 0.1% of MgSO$_4$) to be absorbed by the absorbent resin thereby finding the volume (A ml) of the artificial urine so absorbed, and performing the calculation of the following formula 2.

$$\text{Absorption capacity (ml/g) under load} = A \text{ (ml)}/0.2 \text{ (g)} \quad (2)$$

(c) Water-soluble content

This property was determined by dispersing 0.5 g of a given hydrophilic resin in 1,000 ml of deionized water, stirring the sample in the water for 12 hours, passing the resultant dispersion through a filter paper, finding the weight of solids in the filtrate, and performing the calculation of the following formula 3.

$$\text{Water-soluble content (\%)} = (\text{Weight of filtrate (g)} \times \text{solids in filtrate (\%)})/0.5 \text{ (g)} \quad (3)$$

(d) Suction power

This magnitude was determined by pouring 20 ml of artificial urine over tissue paper thereby preparing a substrate material containing the artificial urine, placing 1 g of a given absorbent resin on the substrate material and, after the elapse of 10 minutes, collecting a swollen gel, and weighing the gel thereby finding the ratio of the weight of urine to the weight of tissue paper (g/g).

(e) Amount of liquid absorbed under load

This magnitude, i.e. the amount of artificial urine (g) absorbed under load, was determined by securing a commercially available infant disposable diaper (L size), removing the core of the diaper, inserting as a replacement therefor a core having 7.5 g of a given absorbent resin buried in 30 g of a wad of pulp thereby completing a test diaper ($W_0$ g), keeping the test diaper immersed for 60 minutes in artificial urine kept under a load of 20 g/cm$^2$, removing the wet diaper from the artificial urine, straining the urine out of the wet diaper, weighing the diaper to find the weight ($W_1$ g), and finding the amount of the artificial urine (g) absorbed by the diaper under the pressure mentioned above by subtracting $W_0$ from $W_1$.

The esters containing a structural unit represented by the general formula (I) will be referred to collectively as "$\beta$-acryloyloxy propionate ($\beta$-AP)." The changing points of the relevant cross-linked polymers are generally found to start in the range of from 120° to 200° C.

EXAMPLE 1

An aqueous monomer solution having a monomer concentration of 37% and a neutralization ratio of 75% was obtained by combining 90 g of acrylic acid and 956 g of an aqueous 37 wt % sodium acrylate solution as hydrophilic unsaturated monomers with 1.47 g (0.05 mol %) of trimethylol propane tri($\beta$-acryloyloxy propionate) as a cross-linking agent (1) and 145 g of deionized water.

Then, a reaction vessel prepared by furnishing a lid for a jacketed twin-arm type stainless steel kneader having an inner volume of 2.5 liters and provided with two sigma type vanes was charged with the aqueous monomer solution mentioned above and swept with nitrogen gas to displace the entrapped air.

Further, 0.1 mol % of ammonium persulfate and 0.01 mol % of sodium hydrogen sulfite were added as polymerization initiators to the reaction vessel, with the two sigma type vanes kept in rotation and the jacket warmed by passage of hot water at 30° C. The monomers in the reaction vessel began to polymerize one minute after the addition of the polymerization initiators. The peak temperature in the reaction system reached 83° C. eight minutes after the addition of the polymerization initiators. The hydrated gel polymer had been finely divided into particles about 5 mm in diameter by then. The stirring of the reaction system continued for a further 60 minutes following the initiation of the polymerization. Then, the reaction vessel was opened by removing the stopper to obtain a hydrated gel polymer cross-linked with trimethylol propane tri($\beta$-acryloyloxy propionate).

The hydrated gel polymer was spread out on a metallic net and dried thereon with hot air at 150° C. for 90 minutes to dry and, at the same time, heat-treat the cross-linked polymer. The dry polymer was pulverized with a shaking mill and sifted to obtain an absorbent resin (1) having a particle size of not more than 20 mesh. The results are shown in Table 1.

EXAMPLE 2

An absorbent resin (2) was obtained by repeating the procedure of Example 1, except that the heat-treatment of the hydrated gel polymer was carried out with the drying temperature changed from 150° C. to 180° C.

Due to the elevation in the temperature of the heat-treatment from 150° C. to 180° C., the produced absorbent resin (2) showed an amply increased absorption capacity. The results are shown in Table 1.

EXAMPLE 3

The procedure of Example 1 was repeated, except that 1.60 g (0.05 mol %) of polyethylene glycol di($\beta$-acryloyloxy propionate) was used in the place of the trimethylol propane tri($\beta$-acryloyl-oxy propionate) as the cross-linking agent (1) for the preparation of monomer.

Then, the resultant aqueous monomer solution was polymerized in the same manner as in Example 1 to obtain a hydrated gel polymer cross-linked with polyethylene glycol di($\beta$-acryloyloxy propionate). This hydrated gel polymer was dried in the same manner as in Example 1 to dry and, at the same time, heat-treating the cross-linked polymer. The dried polymer was pulverized and sifted to obtain an absorbent resin (3). The results are shown in Table 1.

EXAMPLE 4

An absorbent resin (4) was obtained by following the procedure of Example 3, except that the temperature of the heat-treatment for drying the hydrated gel polymer was changed from 150° C. to 110° C.

Due to the decrease in the temperature of heat treatment of the cross-linked polymer from 150° C. to 110° C., the produced absorbent resin (4) showed a large fall of the absorption capacity. The results are shown in Table 1.

EXAMPLE 5

An absorbent resin (5) was obtained by following the procedure of Example 1, except that the temperature of the heat-treatment for drying the hydrated gel polymer was changed from 150° C. to 110° C. The results are shown in Table 1.

EXAMPLE 6

The procedure of Example 1 was repeated, except that 0.47 g (0.02 mol % based on the monomer) was used in the place of the trimethylol propane tri($\beta$-acryloyloxy propionate) as the cross-linking agent (1) for the preparation of the monomer and, at the same time, 0.06 g (0.004 mol %)- of glycerol triacrylate was additionally used as a second cross-linking agent for the adjustment of cross-linked density.

Then, the resultant aqueous monomer solution was polymerized in the same manner as in Example 1 to obtain a hydrated gel polymer cross-linked with glycerol tri ($\beta$-acryloyloxy propionate) and glycerol triacrylate. Subsequently, this hydrated gel polymer was dried at 150° C. in the same manner as in Example 1 to dry and, at the same time, heat treat the cross-linked polymer. The dried polymer was pulverized and sifted to obtain an absorbent resin (6). The results are shown in Table 1.

EXAMPLE 7

An absorbent resin (7) was obtained by following the procedure of Example 6, except that the heat treatment for drying the hydrated gel polymer was carried out at 110° C. for 120 minutes. The results are shown in Table 1.

EXAMPLE 8

The procedure of Example 1 was repeated, except that 3.21 g (0.1 mol % based on the monomer) of pentaerythritol tetra($\beta$-acryloyloxy propionate) was used in the place of the trimethylol propane tri($\beta$-acryloyloxy propionate) as the cross-linking agent (1) for the adjustment of the monomer.

Then, the resultant aqueous monomer solution was polymerized in the same manner as in Example 1 to obtain a hydrated gel polymer cross-linked with pentaerythritol tetra($\beta$-acryloyloxy propionate). Subsequently, this hydrated gel polymer was dried in the same manner as in Example 1 to dry and, at the same time, heat treat the cross-linked polymer. Further, the resultant dried polymer was pulverized and sifted to obtain an absorbent resin (8).

Due to the increase in the amount of the cross-linking agent to 0.1 mol %, the produced hydrated gel polymer showed a further fall in the viscosity and, the gel was uniformly and more finely pulverized.

The results are shown in Table 1.

EXAMPLE 9

An aqueous monomer solution having a neutralization ratio of 70% and a monomer concentration of 35% was obtained by combining 259 g of acrylic acid and 2,136 g of an aqueous 37% sodium acrylate solution as hydrophilic unsaturated monomers with 5.8 g (0.2 mol % based on the monomers) of ethylene glycol monoacrylate mono($\beta$-acryloyloxy propionate) as a cross-linking agent (1) and 605 g of deionized water.

This aqueous monomer solution was deaerated with nitrogen and placed in a switching cast polymerization apparatus having an inner volume of 300 mm×300 mm×50 mm and having the interior thereof displaced with nitrogen. The apparatus containing the aqueous monomer solution was immersed in a water bath kept at 30° C. Further, 0.05 mol % of ammonium persulfate and 0.02 mol % of sodium hydrogen sulfite were added to the apparatus. The monomer in the apparatus was allowed to polymerize. After the elapse of five hours from the start of polymerization, the produced hydrated gel polymer was extracted from the cast polymerization apparatus.

The hydrated gel polymer consequently obtained as cross-linked with ethylene glycol monoacrylate mono($\beta$-acryloyloxy propionate) was finely divided into particles and then dried in the same manner as in Example 1 to dry and, at the same time, heat treat the polymer. Further, the dried polymer was pulverized and sifted to obtain an absorbent resin (9). The results are shown in Table 1.

EXAMPLE 10

An aqueous monomer solution having a monomer concentration of 35% and a neutralization ratio of 75% was obtained by combining 7.21 g of acrylic acid and 76.2 g of an aqueous 37 wt % sodium acrylate solution as hydrophilic unsaturated monomers with 0.036 g (0.02 mol %) of tetraethylene glycol di($\beta$-acryloyloxy propionate) as a cross-linking agent and 17.77 g of deionized water. Further, this aqueous monomer solution, with 0.06 mol % of potassium persulfate dissolved therein, was washed with a forced current of nitrogen gas to expel the dissolved oxygen.

In a four-neck separable flask provided with a stirrer, a reflux condenser, a thermometer, a nitrogen gas inlet tube, and a dropping funnel and having an inner volume of 500 ml, 250 ml of cyclohexane was placed and 2.0 g of sorbitan monostearate (HLB 4.7) as a dispersant was dissolved therein and the resultant mixture was washed with a forced current of air to expel the dissolved oxygen.

Then, the aqueous monomer solution was dispersed in the mixture held in the separable flask. The bath was heated to 60° C. to start polymerization of the monomer. The reaction system was kept at this temperature for 2 hours to complete the polymerization.

After the polymerization, the hydrated gel polymer produced consequently as cross-linked with tetraethylene glycol di($\beta$-acryloyloxy propionate) was filtered and further dried at 130° C. under a vacuum for 1 hour to obtain an absorbent resin(10). The results are shown in Table 1.

EXAMPLE 11

An aqueous monomer solution having 25% of monomer concentration and 100% of neutralization ratio was obtained by adding 81.1 g of 37% by weight of sodium acrylate as a hydrophilic unsaturated monomer and 0.018 g of polyethylene glycol di($\beta$-acryloyloxy propionate) (0.01 mol % to the monomer) into 38.9 g of deionized water.

Then the aqueous monomer solution was poured into a cylindrical container having 9 cm of an inner diameter filled with nitrogen gas after substitution, heated at a temperature of 30° C., and 0.005 mol % of sodium persulfate and 0.001 mol % of 1-ascorbic acid as polymerization initiators to initiate the polymerization gradually and to gel. After 6 hours from the initiation of polymerization, gelled polymer was removed and was cut to about 1–4 mm of diameter by a scissors.

The gelled polymer was water-insoluble and cross-linked, and then heat-treated by drying in an oven maintained at 160° C. for 1 hour. Then the dried polymer was pulverized by a table crusher to obtain a hydrophilic resin (11) by classifying the powder passed a sieve having 850 $\mu$m of mesh. 0.5 g of the hydrophilic resin thus obtained was dispersed into 1 liter of deionized water to find that it was completely dissoloved into water and water-soluble.

EXAMPLE 12

The powdery absorbent resin (1) obtained in Example 1 was heated at 190° C. for 1 hour to effect a further heat treatment of the cross-linked polymer.

As a result, an absorbent resin (12) having an absorption capacity of 88 g/g was obtained from the absorbent resin (1) which had an absorption capacity of 76 g/g. The results are shown in Table 1.

EXAMPLE 13

The powdery absorbent resin (5) obtained in Example 5 was heated at 190° C. for 30 minutes to effect further heat-treatment of the cross-linked polymer.

As a result, an absorbent resin (13) having an absorption capacity of 77 g/g was obtained from the absorbent resin (5) which had an absorption capacity of 45 g/g. The results are shown in Table 1.

EXAMPLE 14

The powdery absorbent resin (4) obtained in Example 4 was heated at 180° C. for ten minutes to effect further heat-treatment of the cross-linked polymer.

As a result, an absorbent resin (14) having an absorption capacity of 87 g/g was obtained from the absorbent resin (4) which had an absorption capacity of 48 g/g. The results are shown in Table 1.

EXAMPLE 15

The powdery absorbent resin (4) was heat-treated in the same manner as in Example 13, except that the duration of the heat treatment was extended from ten minutes to 30 minutes to effect further heat treatment of the cross-linked polymer.

As a result, an absorbent resin (15) having an absorption capacity of 104 g/g was obtained from the absorbent resin (4) which had an absorption capacity of 48 g/g. The results are shown in Table 1.

EXAMPLE 16

The powdery absorbent resin (7) obtained in Example 7 was heated at 160° C. for 30 minutes to effect further heat treatment of the cross-linked polymer.

As a result, an absorbent resin (16) having an absorbent ratio of 62 g/g was obtained from the absorbent resin (7) which had an absorption capacity of 51 g/g. The results are shown in Table 1.

Example 17

The powdery absorbent resin (7) was heat treated in the same manner as in Example 15, except that the temperature of the heat treatment was changed from 160° C. to 175° C. for effecting further heat treatment of the cross-linked polymer.

As a result, an absorbent resin (17) having an absorption capacity of 65 g/g was obtained from the absorbent resin (7) which had an absorption capacity of 51 g/g. The results are shown in Table 1.

Example 18

The powdery absorbent resin (7) was heat treated in the same manner as in Example 15, except that the temperature of the heat treatment was changed from 160° C. to 200° C.

As a result, an absorbent resin (18) having an absorption capacity of 72 g/g was obtained from the absorbent resin (7) which had an absorption capacity of 51 g/g. The results are shown in Table 1.

Control 1

The procedure of Example 1 was repeated, except that the trimethylol propane tri($\beta$-acryloyloxy propionate) used as the cross-linking agent (1) for the preparation of the monomer was changed to the same mol number, i.e. 0.67 g (0.05 mol % based on the monomer), of trimethylol propane triacrylate.

Then, the aqueous monomer solution using the changed cross-linking agent was polymerized in the same manner as in Example 1 and dried at 150° C. Further, the dried polymer was pulverized and sifted to obtain an absorbent resin (1) for comparison.

The absorption capacity of the absorbent resin (1) for comparison was noticeably lower than that of the absorbent resin (1). The results are shown in Table 2.

Control 2

An absorbent resin (2) for comparison was obtained by following the procedure of Control 1, except that the temperature of the heat treatment for drying the produced hydrated gel polymer was changed from 150° C. to 180° C. to effect heat treatment of the cross-linked polymer.

The hydrated gel polymers obtained in Controls 1 and 2 as cross-linked with the same cross-linking agent, trimethylol propane triacrylate showed virtually no change in absorption capacity even when the temperature of heat treatment was elevated from 150° C. to 180° C. The results are shown in Table 2.

Control 3

The procedure of Example 3 was repeated, except that the polyethylene glycol di($\beta$-acryloyloxy propionate) used as the cross-linking agent (1) for the preparation of the monomer was changed to the same mol number, i.e. 1.20 g (0.05 mol %), of polyethylene glycol diacrylate.

Then, the resultant aqueous monomer solution using the changed cross-linking agent was polymerized in the same manner as in Example 3 and pulverized and sifted to obtain an absorbent resin (3) for comparison. The absorption capacity of the absorbent resin (3) for comparison was noticeably lower than that of the absorbent resin (3). The results are shown in Table 2.

Controls 4 and 5

The procedure of Control 1 was repeated, except that the amount of the cross-linking agent, trimethylol propane triacrylate, used was changed to 0.01 mol % (Control 4) or 0.005 mol % (Control 5) to lower the cross-linked density during the polymerization and consequently obtain the same absorption capacity as in Example 1. Then, the aqueous monomer solutions using different kinds of cross-linking agent were polymerized in the same manner as in Example 1 and dried, pulverized, and sifted to obtain absorbent resins (4) and (5) for comparison.

The gels consequently obtained were so soft as to adhere heavily to the polymerization vessel and allow no sufficient disintegration because the amounts of crosslinking agent used during the polymerization were small. This inclination was more conspicuous when the amount of the cross-linking agent was 0.005 mol %. Because of the insufficient gel disintegration, the work of drying required three hours. The absorbent resins (4) and (5) for comparison thus obtained showed great increases in the soluble content as compared with the resin of Example 1. The results are shown in Table 2.

Control 6

The procedure of Control 3 was repeated, except that the polymerization was carried out without using any crosslinking agent for the purpose of attaining the same absorption capacity as in Example 3.

The hydrated gel polymers obtained without using any cross-linking agent were soft gels of extremely high viscosity. It was scarcely pulverized by vigorous kneading with the rotation of the stirring shaft and the polymerization proceeded non-uniformly. The stirring was further continued to complete the polymerization 60 minutes after the start of polymerization. The produced hydrated gel polymer was in the form of lumps deposited so fast to the vessel as to be difficult to remove.

When the lumps of hydrated gel were dried with hot air in the same manner as in Example 1, 6 hours were required for them to be substantially dried.

The absorbent resin (6) for comparison thus obtained had a remarkably larger soluble content than the absorbent resin of Example 3 and showed a low absorption capacity. The results are shown in Table 2.

Control 7

An absorbent resin (7) for comparison was obtained by following the procedure of Example 12, except that the cross-linking agent used in Example 6 was changed to the same mol number (0.025 mol) of glycerol triacrylate. The results are shown in Table 2.

Control 8

An absorbent resin (8) for comparison was obtained by following the procedure of Example 9, except that the cross-linking agent was changed to the same mol number of N,N'-methylene bis-acrylamide.

The production of the resin was easy to carry out because the amount of the cross-linking agent used was 0.2 mol %, a large volume in the normal measure, though the absorption capacity was only 29 g/g, an extremely low level in any measure. The results are shown in Table 2.

Control 9

An absorbent resin (9) for comparison was obtained by following the procedure of Example 9, except that the amount of the cross-linking agent used in Control 7 was changed to 0.02 mol %.

Because of the small amount of the cross-linking agent, the absorbent resin was difficult to extract from the polymerization vessel and was difficult to pulverize with a meat chopper and dried unevenly. The results are shown in Table 2.

Control 10

An absorbent resin (10) for comparison was obtained by heat treating the powdery absorbent resin (1) for comparison of Control 1 at 190° C. for one hour. When the cross-linked polymer was heat-treated, it showed to change in its absorption capacity. The results are shown in Table 2.

Controls 11 to 13

Absorbent resins (11) to (13) for comparison were obtained by repeating the procedures of Examples 15 to 17 respectively, except that the absorbent resin (7) for comparison obtained in Control 7 was used in the place of the absorbent resin (7). In spite of the heat-treatment of the powdery polymer, they show virtually no change in absorption capacity. The results are shown in Table 2.

Control 14

An absorbent resin (14) for comparison was obtained by subjecting the powdery absorbent resin (8) for comparison obtained in Control 8 to a heat treatment at 150° C. for 8 hours. The cross-linked polymer showed no change in absorption capacity even when it was heat treated. The results are shown in Table 2.

TABLE 1

| Example | Cross-linking agent | Amount used (mol %) | Disintergration (aggregation) of gell | State of cross-linked polymer during heat-treatment | Temperature (°C.) | Time (min) | Absorption capacity (g/g) | Soluble content (%) |
| --- | --- | --- | --- | --- | --- | --- | --- | --- |
| 1 | TMPT (β-AP) | 0.05 | ◎ | Polymer gel | 150 | 90 | 76 | 18 |
| 2 | ↑ | ↑ | ◎ | ↑ | 180 | ↑ | 95 | 30 |
| 3 | PEGJ (β-AP) | 0.05 | ◎ | ↑ | 150 | ↑ | 109 | 47 |
| 4 | ↑ | ↑ | ◎ | ↑ | 110 | ↑ | 48 | 6 |
| 5 | TMPT (β-AP) | 0.05 | ◎ | ↑ | 110 | ↑ | 45 | 4 |
| 6 | GlyT (β-AP)/ GlyTA | 0.02/ 0.005 | ○ | ↑ | 150 | 90 | 70 | 14 |
| 7 | ↑ | ↑ | ○ | ↑ | 110 | 120 | 51 | 6 |
| 8 | PTET (β-AP) | 0.1 | ◎ | ↑ | 150 | 90 | 56 | 13 |
| 9 | EGA (β-AP) | 0.2 | ◎ | ↑ | 150 | ↑ | 46 | 7 |
| 10 | TEGJ (β-AP) | 0.02 | ○~△ | ↑ | 130 | 60 | 91 | 27 |
| 12 | TMPT (β-AP) | 0.05 | | Powder of (1) | 190 | 60 | 88 | 24 |
| 13 | ↑ | ↑ | | Powder of (5) | 190 | 30 | 77 | 19 |
| 14 | PEGJ (β-AP) | 0.05 | | Powder of (4) | 180 | 10 | 88 | 26 |
| 15 | ↑ | ↑ | | ↑ | 180 | 30 | 104 | 43 |
| 16 | GlyT (β-AP)/ GlyTA | 0.02/ 0.005 | | Powder of (7) | 160 | 30 | 62 | 16 |
| 17 | ↑ | ↑ | | ↑ | 175 | ↑ | 65 | 16 |
| 18 | ↑ | ↑ | | ↑ | 200 | ↑ | 71 | 17 | was changed to 0.02 mol %.

TABLE 2

| Control | Cross-linking agent | Amount used (mol %) | Disintergration (aggregation) of gell | State of cross-linked polymer during heat-treatment | Temperature (°C.) | Time (min) | Absorption capacity (g/g) | Soluble content (%) |
| --- | --- | --- | --- | --- | --- | --- | --- | --- |
| 1 | TMPTA | 0.05 | ◎ | Polymer gel | 150 | 90 | 50 | 9 |
| 2 | ↑ | ↑ | ↑ | ↑ | 180 | ↑ | 51 | 11 |
| 3 | PEGJA | 0.05 | ◎ | ↑ | 150 | ↑ | 52 | 11 |
| 4 | TMPTA | 0.01 | △~X | ↑ | ↑ | 180 | 74 | 39 |
| 5 | ↑ | 0.005 | △~X | ↑ | ↑ | ↑ | 78 | 45 |
| 6 | (None) | (None) | X | ↑ | ↑ | 360 | 88 | 66 |
| 7 | GlyTA | 0.025 | ○ | ↑ | 110 | 120 | 44 | 6 |
| 8 | MBAA | 0.2 | ◎ | ↑ | 150 | ↑ | 29 | 2 |
| 9 | ↑ | 0.02 | ○~△ | ↑ | ↑ | ↑ | 48 | 12 |
| 10 | TMPTA | 0.05 | | Powder of Control (1) | 190 | 60 | 50 | 9 |

TABLE 2-continued

| | | | | | | | |
|---|---|---|---|---|---|---|---|
| 11 | GlyTA | 0.025 | Powder of Control (7) | 160 | 30 | 44 | 6 |
| 12 | ↑ | ↑ | ↑ | 175 | ↑ | 45 | 7 |
| 13 | ↑ | ↑ | ↑ | 190 | ↑ | 45 | 7 |
| 14 | MBAA | 0.2 | Powder of Control (9) | 150 | 480 | 29 | 2 |

| Code | Cross-linking agent |
|---|---|
| TMPT (β-AP) | Trimethylol propane tri(β-acryloyloxy propionate) |
| PEG (β-AP) | Polyethylene glycol di(β-acryloyloxy propionate) |
| GlyT (β-AP) | Glycerol tri(β-acryloyloxy propionate) |
| PTET (β-AP) | Pentaerythritol tetra(β-acryloyloxy propionate) |
| EGA (β-AP) | Ethylene glycol monoacrylate mono(β-acryloyloxy propionate) |
| TEG (β-AP) | Tetraethylene glycol di(β-acryloyloxy propionate) |
| TMPTA | Trimethylol propane triacrylate |
| PEGJA | Polyethylene glycol diacrylate |
| GlyTA | Glycerol triacrylate |
| MBAA | N,N'-methylenebis acrylamide |

For rating the state of gel disintegration (aggregation)
◎: Extremely desirable disintegration with virtually no adhesion or aggregation
○: Desirable disintegration with sparing adhesion or aggregation
△: Undesirable disintegration with appreciable adhesion or aggregation
X: Conspicuous adhesion and aggregation and sparing or absolutely no pulverization It is clearly noted from Table 1 that many advantages such as, for example:

(1) The heat-treatment of a gel or powder gives rise to an absorbent resin of high absorption capacity.
(2) The cross-linking effected to a high degree during the polymerization facilitates the polymerization and the subsequent steps of the process of production.
(3) The adjustment of the temperature and duration of the heat treatment performed on the powder allows desired alteration of the absorption capacity over a wide range.
(4) The water-soluble content is small for the fixed level of absorption capacity.

These advantages are derived by heightening the cross-linked density with the cross-linking agent (1) and further performing a heat treatment after the polymerization thereby attaining the required physical properties.

EXAMPLE 19

A mixture containing 414 g of acrylic acid and 4,382 g of an aqueous 37 wt % sodium acrylate solution as hydrophilic unsaturated monomers, 7.14 g (0.05 mol %) of polyethylene glycol di(β-acryloyloxy propionate) as a cross-linking agent (1), and 669 g of deionized water was supplied to a reaction vessel prepared by furnishing a stopper to a jacketed twin-arm type stainless steel kneader having an inner volume of 10 liters and provided with two sigma-type vanes. The monomers in the reaction vessel were kept at 30 °C. and the air entrapped in the reaction system was displaced with nitrogen gas. When the mixture in the reaction vessel was kept stirred and 2.76 g of ammonium persulfate and 0.12 g of 1-ascorbic acid were added thereto, polymerization of the monomers started one minute after the addition. The stirring continued further. After the elapse of 60 minutes from the start of polymerization, the hydrated gel polymer consequently formed was extracted from the reaction vessel. The minute particles of the hydrated gel polymer thus obtained were spread out on a 50-mesh metallic net and dried thereon with hot air at 130° C. for 90 minutes. The dried polymer was pulverized with a shaking mill and sifted with a 20-mesh screen to obtain a water-swellable cross-linked polymer (1) of the shape of irregularly broken fragments having a water content of 8%, an average particle diameter of 370 μm, and an absorption capacity of 49 g/g with respect to physiological saline solution.

A mixture consisting of 100 parts of the water-swellable cross-linked polymer (1), 1 part of glycerol as a cross-linking agent (3), 3 parts of water, and 1 part of isopropyl alcohol was heat- treated at 195° C. for 25 minutes. The absorbent resin (19) consequently obtained was tested for quality. The results are shown in Table 3.

EXAMPLE 20

A mixture containing 100 parts of the water-swellable cross-linked polymer (1) obtained in Example 19, 0.1 part of ethylene glycol diglycidyl ether as a crosslinking agent (3), 6 parts of water, and 1 part of ethyl alcohol was heat-treated at 180° C. for ten minutes. The absorbent resin (20) consequently obtained was tested for quality. The results of the test are shown in Table 3.

Example 21

The polymerization of Example 19 was repeated, except that 5.88 g (0.05 mol %) of trimethylol propane tri(β-cryloyloxy propionate) was used as a cross-linking agent (1) in the place of the polyethylene glycol .di(β-acryloyloxy propionate). The polymerization was followed by a hot-air drying which was performed at 120° C. for 120 minutes. The dried polymer was pulverized and sifted in the same manner as in Example 19, to obtain a water-swellable cross-linked polymer (2) of the shape of irregularly broken fragments having a water content of 12%, an average particle diameter of 410 μm, and an absorption capacity of 47 g/g with respect to physiological saline solution.

Then, a mixture containing 100 parts of the water-swellable cross-linked polymer (2), 1 part of propylene glycol as a cross-linking agent (3), 3 parts of water, and 2 parts of methyl alcohol was heat treated at 195° C. for 20 minutes. The absorbent resin (21) consequently obtained was tested for quality. The results of the test are shown in Table 3.

EXAMPLE 22

A mixture was obtained by mixing 100 parts of the water-swellable cross-linked polymer (2) obtained in Example 20 with a liquid cross-linking agent composition of 0.2 part of glycerol triglycidyl ether as a cross-linking agent (3), 5 parts of water, and 2 parts of methanol. This mixture was heat treated at 150° C. for 50 minutes. The absorbent resin (22) consequently obtained was tested for quality. The results of the test are shown in Table 3.

EXAMPLE 23

The polymerization of Example 19 was repeated, except that 2.53 g (0.02 mol %) of polyethylene glycol mono(β-acryloyloxy propionate) monoacrylate (average PEG chain 8) was used as a cross-linking agent (1) in the place of the polyethylene glycol di(β-acryloyloxy propionate) (average PEG chain 8) and 0.71 g (0.02 mol %) of N,N'-methylene bisacrylamide was used as a cross-linking agent (2). The polymerization was followed by hot-air drying performed at 140° C. for 90 minutes. The dried polymer was pulverized and sifted in the same manner as in Example 18, to obtain a water-swellable cross-linked polymer (3) of the shape of irregularly-broken fragments having a water content of 5%, an average particle diameter of 360 μm, and an absorption capacity of 58 g/g with respect to physiological saline solution. A mixture obtained by combining 100 parts of the water-swellable cross-linked polymer (3) with 1.5 parts of ethylene carbonate as a cross-linking agent (2), 3 parts of water, and 2 parts of methanol. This mixture was heat treated at 180° C. for 60 minutes. The absorbent resin (23) consequently obtained was tested for quality. The results of the test are shown in Table 3.

Control 15

The polymerization of Example 18 was repeated, except that 1.77 g (0.05 mol %) of N,N'-methylene bisacrylamide was used as a cross-linking agent in the place of the polyethylene glycol di(β-acryloyloxy propionate). The polymerization was followed by hot-air drying performed at 130° C. for 90 minutes. The dried polymer was pulverized and sifted in the same manner as in Example 19 to obtain a water-swellable cross-linked polymer (1) for comparison in the form of irregularly broken fragments having a water content of 5%, an average particle diameter of 380 μm, and an absorption capacity of 46 g/g with respect to physiological saline solution.

A mixture was obtained by combining 100 parts of the water-swellable cross-linked polymer (1) for comparison with 1 part of glycerol as a cross-linking agent (3), 3 parts of water, and 1 part of isopropyl alcohol. This mixture was heat treated at 195° C. for 30 minutes. The absorbent resin (15) for comparison consequently obtained was tested for quality. The results of the test are shown in Table 4.

Control 16

The water-swellable cross-linked polymer (1) obtained in Example 19, with no liquid cross-linking agent composition added thereto, was heat-treated at 180° C. for 30 minutes. The absorbent resin (16) for comparison consequently obtained was tested for quality. The results of the test are shown in Table 3.

Control 17

The polymerization of Example 1 was repeated, except that 0.18 g (0.005 mol %) of N,N'-methylene bisacrylamide was used as a cross-linking agent in the place of the polyethylene glycol di(β-acryloyloxy propionate). The polymerization was followed by hot-air drying performed at 130° C. for 90 minutes. The dried polymer was pulverized and sifted in the same manner as in Example 1 to obtain a water-swelling cross-linked polymer (2) for comparison in the shape of irregularly broken fragments having a water content of 5%, an average particle diameter of 430 μm, and an absorption capacity of 78 g/g with respect to physiological saline solution.

A mixture was obtained by combining 100 parts of the water-swellable cross-linked polymer (2) for comparison with a liquid composition of 1 part of glycerol as a cross-linking agent (3), 3 parts of water, and 1 part of isopropyl alcohol. This mixture was heat treated at 195° C. for 30 minutes. The absorbent resin (17) for comparison consequently obtained was tested for quality. The results of the test are shown in Table 3.

TABLE 3

| | Absorption ratio (g/g) | Absorption ratio under loading (ml/g) | Suction power (g/g) | Amount of absorption by absorbent resin under loading (g) |
|---|---|---|---|---|
| Absorbent resin (19) | 65 | 32 | 18 | 582 |
| Absorbent resin (20) | 57 | 33 | 17 | 604 |
| Absorbent resin (21) | 50 | 33 | 17 | 572 |
| Absorbent resin (22) | 52 | 32 | 18 | 591 |
| Absorbent resin (23) | 61 | 31 | 17 | 571 |
| Absorbent resin (15) for comparison | 40 | 26 | 16 | 545 |
| Absorbent resin (16) for comparison | 98 | 10 | 9 | 477 |
| Absorbent resin (17) for comparison | 63 | 28 | 16 | 532 |

What is claimed is:

1. A method for the production of a hydrophilic resin comprising the steps of copolymerizing a hydrophilic unsaturated monomer with 0.001 to 50 mol %, based on the amount of said monomer, of a first cross-linking agent having a structural unit represented by the formula (I):

wherein n represents an integer of at least 1 and then heat-treating the product of said copolymerization.

2. A method according to claim 1, wherein said heat treatment is carried out at a temperature in the range of 100° to 300° C.

3. A method according to claim 2, wherein the hydrophilic resin obtained by said heat-treatment is an absorbent resin having an absorption capacity of 20 to 120 g/g with respect to physiological saline solution.

4. A method according to claim 2, wherein the hydrophilic resin obtained by said heat-treatment is a water-soluble resin containing a water soluble component at a concentration in the range of 80 to 100% by Weight based on the weight of said hydrophilic resin.

5. A method according to claim 1, wherein said first cross-linking agent is the product of esterification of a compound with an alcohol, said compound being represented by the formula (II):

wherein n represents an integer of at least 1 .

6. A method according to claim 5, wherein said alcohol is a polyhydric alcohol.

7. A method according to claim 1, wherein said cross-linking agent is at least one member selected from the group consisting of polyethylene glycol di($\beta$-acryloyloxy propionate), trimethylolpropane tri($\beta$-acryloyloxy propionate), trimethylolpropane di($\beta$-acryloyloxy propionate), polyethylene glycol mono($\beta$-acryloyloxy propionate) monoacrylate, trimethylolpropane mono($\beta$-acryloyloxy propionate) diacrylate, trimethylopropane di($\beta$-acryloyloxy propionate) monoacrylate, and glycidyl ($\beta$-acryloyloxy propionate).

8. A method according to claim 1, wherein the variable n in said formula (I) is an integer of 1 to 10.

9. A method according to claim 1, wherein said hydrophilic unsaturated monomer is at least one monomer selected from the group consisting of acrylic acid and salts thereof, methacrylic acid and salts thereof, 2-(meth)-acryloyl ethane sulfonic acid and salts thereof, 2-(meth) acryl-amide-2-methyl propane sulfonic acid and salts thereof, $\beta$-acryloyloxy propionic acid and salts thereof, methoxy polyethylene glycol (meth)acrylate, N,N-dimethylaminoethyl (meth)acrylate, and acrylamide.

10. A method according to claim 1, wherein said heat-treatment is carried out at a drying step.

11. A method according to claim 1, wherein said heat treatment is effected by heating said product of copolymerization in the dried form.

12. A method according to claim 1 further comprising a second cross-linking agent in the copolymerization step.

13. A method according to claim 12, wherein the total amount of said first cross-linking agent and said second cross-linking agent accounts for a proportion in the range of 0.001 to 50 mol % based on the amount of said hydrophilic unsaturated monomer.

14. A method according to claim 13, wherein the amount of said second cross-linking agent is not more than 50 mol % based on the amount of said first cross-linking agent.

15. A method for the production of an absorbent resin comprising the steps of:

copolymerizing a hydrophilic unsaturated monomer with 0.001 to 50 mol %, based on the amount of said monomer, of a first cross-linking agent having a structural unit represented by the formula (I):

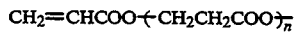
$$CH_2=CHCOO(CH_2CH_2COO)_{\overline{n}} \tag{I}$$

wherein n represents an integer of at least 1 to obtain a hydrophilic resin, adding to the hydrophilic resin a third cross-linking agent capable of reacting with a functional group of said hydrophilic resin, said functional group being derived from said monomer, and reacting said hydrophilic resin, in the surface region of said resin, with said third cross-linking agent.

16. A method according to claim 15, wherein said reaction is carried out under application of heat.

17. A method according to claim 16, wherein said reaction is carried out at a temperature in the range of 100° to 300° C.

18. A method according to claim 15, wherein said first cross-linking agent is the product of an esterification of a compound with an alcohol, said compound being represented by the formula (II):

$$CH_2=CHCOO(CH_2CH_2COO)_{\overline{n}}H \tag{II}$$

wherein n represents an integer of at least 1.

19. A method according to claim 18, wherein said alcohol is a polyhydric alcohol.

20. A method according to claim 15, wherein the variable n in said formula (I) is an integer of 1 to 10.

21. A method according to claim 15, wherein said hydrophilic unsaturated monomer is at least one monomer selected from the group consisting of acrylic acid and salts thereof, methacrylic acid and salts thereof, 2-(meth)acryl ethane sulfonic acid and salts thereof, 2-(meth)acrylamide-2-methyl propane sulfonic acid and salts thereof, $\beta$-acryloyloxy propionic acid and salts thereof, methoxy polyethylene glycol (meth)acrylate, N,N-dimethylaminoethyl (meth) acrylate, and acrylamide.

22. A method according to claim 15, wherein said third cross-linking agent is a compound having in the molecular unit thereof at least two functional groups capable of reacting with the functional group in said hydrophilic resin.

23. A method according to claim 22, wherein the functional group of said hydrophilic resin is a carboxyl group.

24. A method according to claim 15, wherein said third cross-linking agent is used in the presence of at least one member selected from the group consisting of water and hydrophilic organic solvents.

* * * * *